(12) United States Patent
Kelley

(10) Patent No.: US 7,674,251 B2
(45) Date of Patent: Mar. 9, 2010

(54) MEDICAL DEVICES INCLUDING AERATED ADHESIVE BONDS AND METHODS OF FORMING THE SAME

(75) Inventor: Gregory S. Kelley, San Diego, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1330 days.

(21) Appl. No.: 10/820,659

(22) Filed: Apr. 8, 2004

(65) Prior Publication Data
US 2005/0228360 A1    Oct. 13, 2005

(51) Int. Cl.
*A61M 25/00*    (2006.01)
(52) U.S. Cl. .................................................... 604/523
(58) Field of Classification Search ................. 264/494; 604/523, 264, 524, 533
See application file for complete search history.

(56) References Cited

U.S. PATENT DOCUMENTS

| | | | |
|---|---|---|---|
| 4,599,822 A | 7/1986 | Baker | |
| 4,601,724 A | 7/1986 | Hooven et al. | |
| 4,606,782 A | 8/1986 | Demetriades | |
| 4,743,327 A | 5/1988 | DeHaan et al. | |
| 4,846,164 A | 7/1989 | Martz | |
| 4,883,453 A | 11/1989 | Berry et al. | |
| 4,917,112 A | 4/1990 | Kalt | |
| 5,000,741 A | 3/1991 | Kalt | |
| 5,034,165 A | 7/1991 | Willinger et al. | |
| 5,061,258 A | 10/1991 | Martz | |
| 5,074,847 A | 12/1991 | Greenwell et al. | |
| 5,246,451 A | 9/1993 | Trescony et al. | |
| 5,352,322 A | 10/1994 | Leverick | |
| 5,372,589 A | 12/1994 | Davis | |
| 5,451,428 A | 9/1995 | Rupp | |
| 5,491,017 A | 2/1996 | Todt | |
| 5,593,395 A | 1/1997 | Martz | |
| 5,623,812 A | 4/1997 | Todt | |
| 5,700,891 A | 12/1997 | Huver et al. | |
| 5,705,566 A | 1/1998 | Todt | |
| 5,736,231 A | 4/1998 | Todt | |
| 5,789,047 A | 8/1998 | Sasaki et al. | |
| 5,961,498 A | 10/1999 | Wiesendanger | |
| 5,997,517 A | 12/1999 | Whitnourne | |
| 6,013,750 A | 1/2000 | Friese et al. | |
| 6,135,346 A | 10/2000 | Drummond et al. | |
| 6,180,544 B1 * | 1/2001 | Jauchen et al. | .............. 442/150 |
| 6,296,600 B1 | 10/2001 | Drummond et al. | |
| 6,306,176 B1 | 10/2001 | Whitbourne | |
| 6,318,387 B1 | 11/2001 | McClure et al. | |
| 6,319,228 B1 | 11/2001 | Kastenhofer | |
| 6,319,312 B1 | 11/2001 | Luongo | |
| 6,440,226 B2 | 8/2002 | McClure et al. | |
| 6,571,810 B1 | 6/2003 | McClure et al. | |
| 6,659,977 B2 | 12/2003 | Kastenhofer | |
| 2001/0020161 A1 * | 9/2001 | Klima et al. | ................. 604/524 |

(Continued)

*Primary Examiner*—Nicholas D Lucchesi
*Assistant Examiner*—Christopher D Koharski
(74) *Attorney, Agent, or Firm*—Crompton, Seager & Tufte, LLC

(57) ABSTRACT

Medical devices can be formed from medical device components that are bonded together with an adhesive that resists stresses caused by adhesive curing. In particular, a medical device can include a first component and a second component. The second component can be configured to fit at least partially over the first component. An aerated adhesive layer can be formed or disposed between the first and second components.

18 Claims, 5 Drawing Sheets

U.S. PATENT DOCUMENTS

2001/0026666 A1* 10/2001 Ferrera et al. ............... 385/123
2003/0077423 A1* 4/2003 Flanigan et al. ............. 428/166
2004/0064129 A1* 4/2004 Deniega et al. ............. 604/523

* cited by examiner

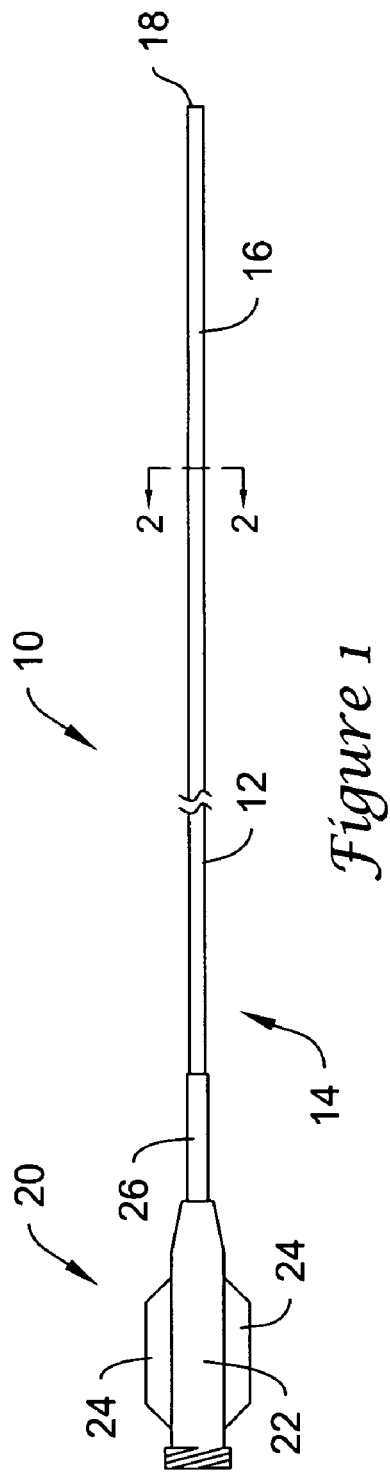
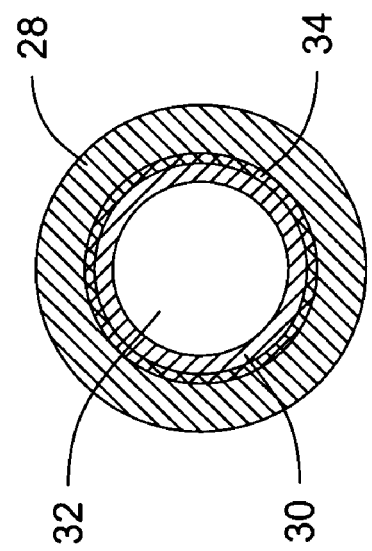

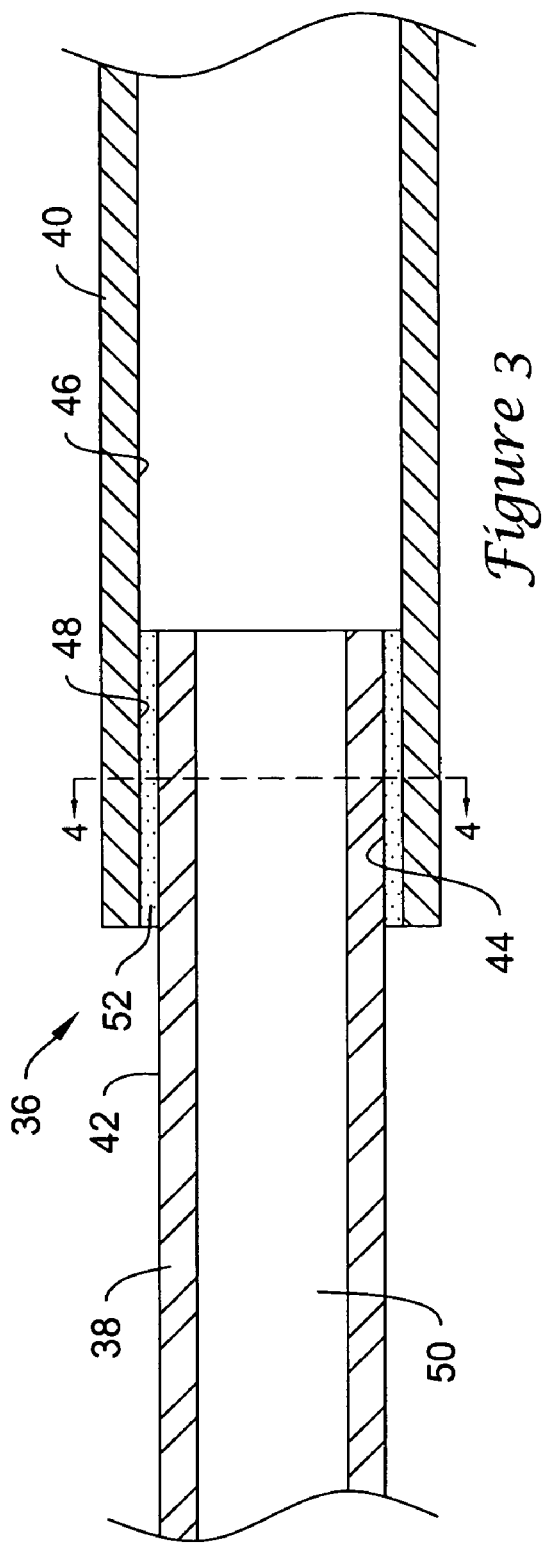
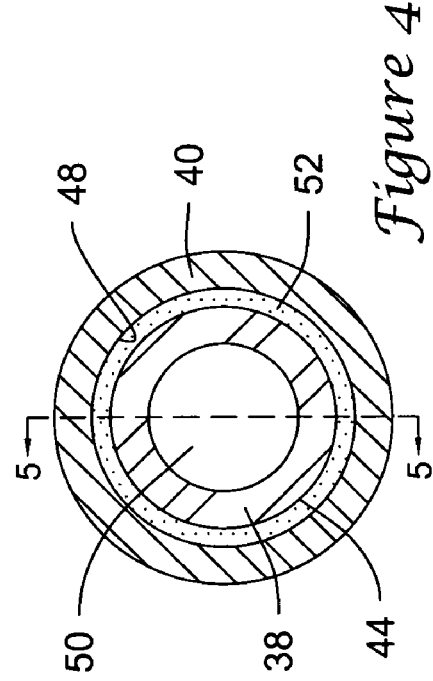

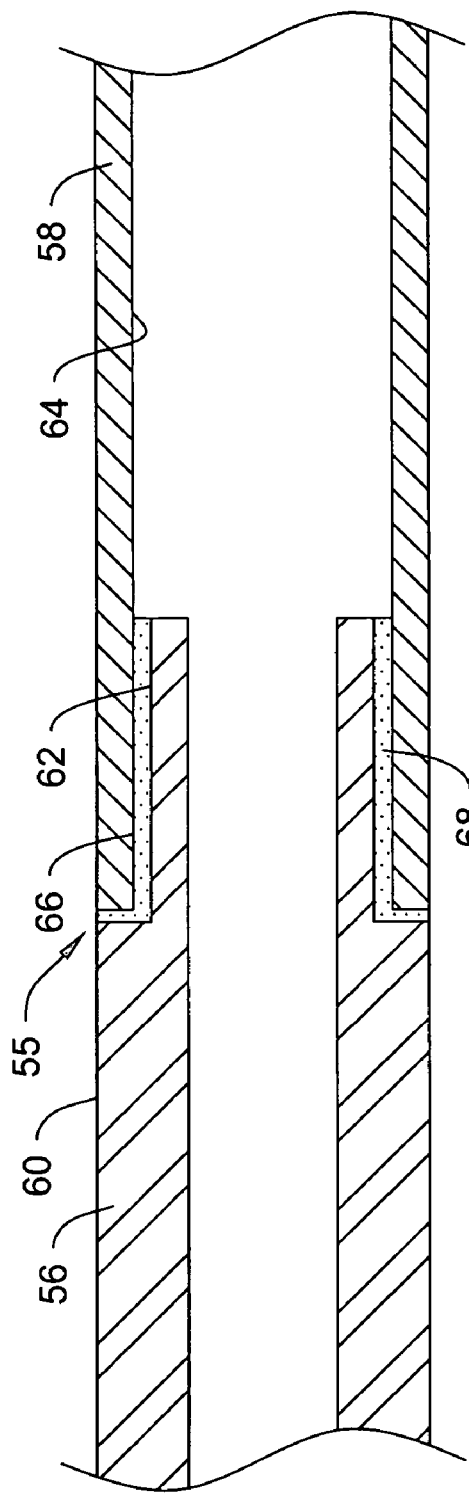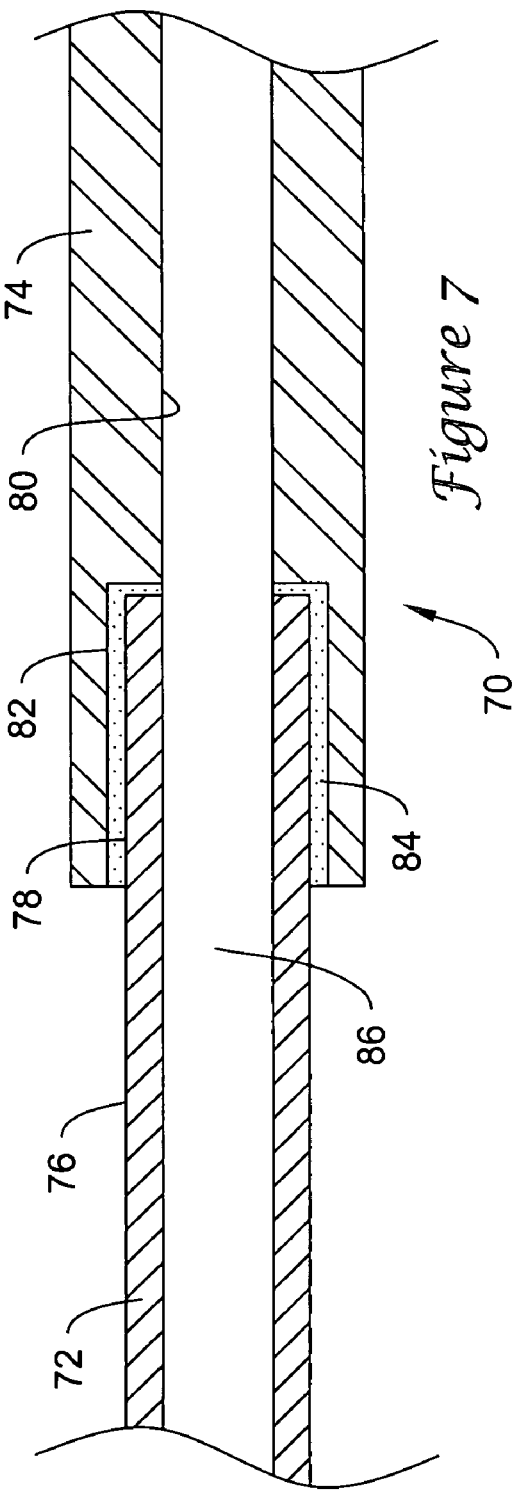

MEDICAL DEVICES INCLUDING AERATED ADHESIVE BONDS AND METHODS OF FORMING THE SAME

TECHNICAL FIELD

The invention relates generally to medical devices and more specifically to medical devices formed by bonding together medical device components. In particular, the invention relates to medical devices formed by bonding together medical device components using aerated adhesives.

BACKGROUND

A variety of medical devices include multiple components that are secured together. In particular, some medical devices such as catheters include multiple components such as an elongate shaft and a hub that is secured to the elongate shaft. Some catheters include luer fittings or other fluid-competent connectors that are secured to the elongate shaft. In some catheters, multiple segments can be joined together to form the elongate shaft. In some catheters, a strain relief is positioned intermediate the hub and the elongate shaft and is secured to both elements.

Medical device components can be secured together using a variety of techniques, including mechanical connections and chemical joining techniques such as adhesives and, in particular, light-cured adhesives. However, light-cured adhesives can exhibit shrinkage upon curing. As the adhesive reduces in volume while curing, stresses can build within the adhesive layer. These stresses can, in some instances, result in delamination between the adhesive layer and each of the components in contact with the adhesive layer.

One solution to this issue is to limit the maximum thickness of the adhesive layer by limiting the gap between the surfaces to be adhesively secured. While this technique can reduce issues with delamination and other adhesive failures, it can place additional demands on the tolerances to which each of the components must be manufactured.

A need remains, therefore, for an improved method of securing medical device components together. A need remains for improved adhesive techniques in forming medical devices.

SUMMARY

The invention is directed to medical devices that are formed from medical device components that are bonded together with an adhesive that resists stresses caused by adhesive curing.

Accordingly, an example embodiment of the invention can be found in a medical device that includes a first component and a second component. The first component has an outer surface that includes an outer engagement portion and the second component has an inner surface that includes an inner engagement portion. The inner engagement portion is configured to fit over the outer engagement portion. An aerated adhesive layer is positioned between the inner engagement portion and the outer engagement portion.

Another example embodiment of the invention can be found in a method of forming a medical device that has a first component with an outer surface and a second component with an inner surface. An aerated adhesive layer is disposed over at least a portion of the outer surface of the first component. The second component is disposed over the first component such that at least a portion of the inner surface contacts the aerated adhesive layer, and the aerated adhesive layer is cured.

Another example embodiment of the invention can be found in a method of forming a medical device that has a first component with an outer surface and a second component with an inner surface. The second component is disposed over the first component such that at least a portion of the inner surface thereof is proximate at least a portion of the outer surface of the first component. An aerated adhesive is injected between the outer surface of the first component and the inner surface of the second component to form an aerated adhesive layer, and the aerated adhesive layer is subsequently cured.

BRIEF DESCRIPTION OF THE DRAWINGS

The invention may be more completely understood in consideration of the following detailed description of various embodiments of the invention in connection with the accompanying drawings, in which:

FIG. 1 is a plan view of an intravascular catheter in accordance with an embodiment of the invention;

FIG. 2 is a cross-sectional view of the intravascular catheter of FIG. 1, taken along the 2-2 line;

FIG. 3 is a partially-sectioned view of a medical device in accordance with an embodiment of the invention;

FIG. 4 is a cross-sectional view of the medical device of FIG. 3, taken along the 4-4 line;

FIG. 6 is a partially-sectioned view of a medical device in accordance with an embodiment of the invention;

FIG. 7 is a partially-sectioned view of a medical device in accordance with an embodiment of the invention.

DETAILED DESCRIPTION

Figure 5:
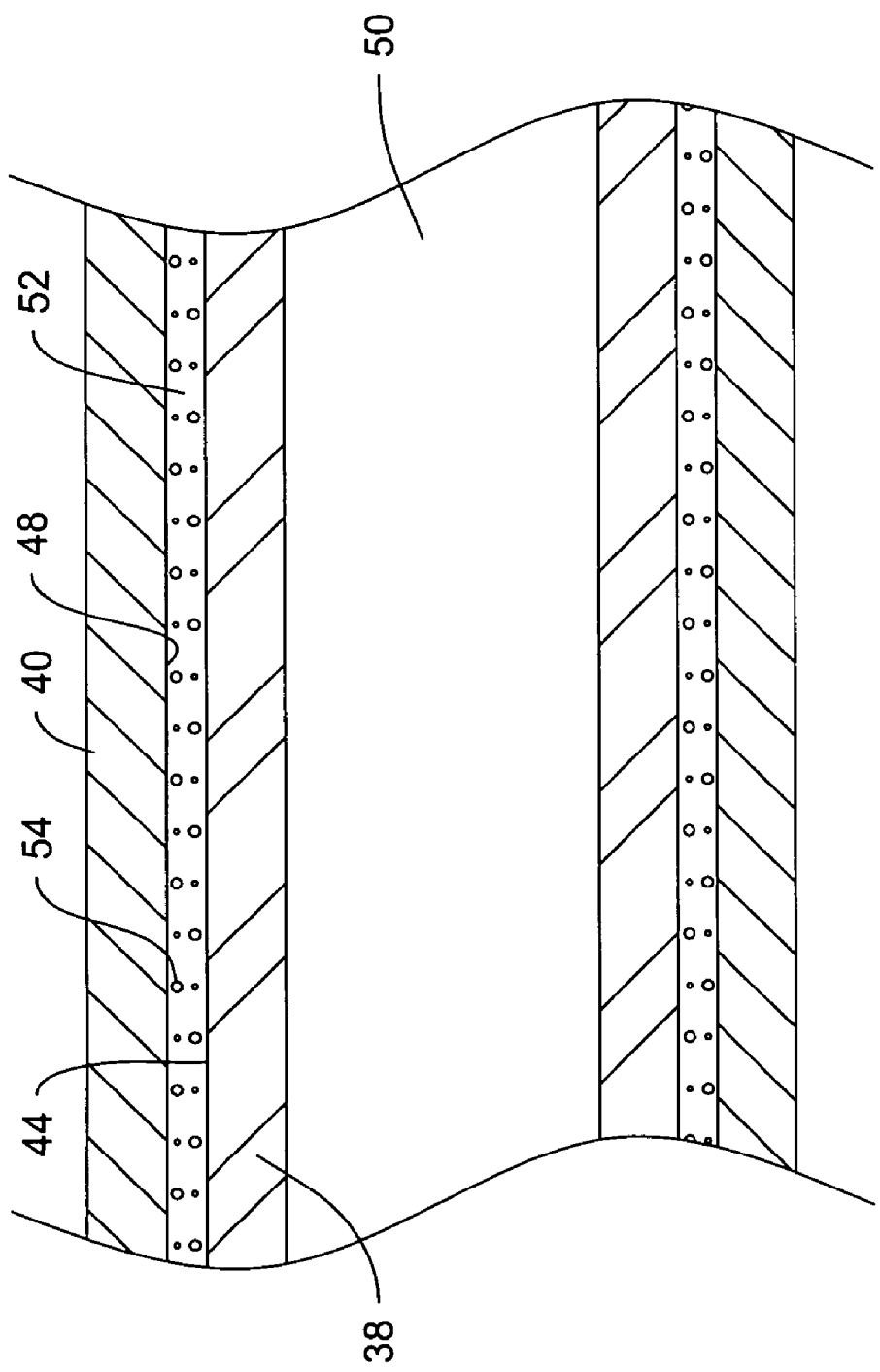
FIG. 5 is a cross-sectional view of the medical device of FIG. 4, taken along the 5-5 line.

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following description should be read with reference to the drawings wherein like reference numerals indicate like elements throughout the several views. The drawings, which are not necessarily to scale, depict illustrative embodiments of the claimed invention.

FIG. 1 is a plan view of a catheter 10 that can be assembled in accordance with an embodiment of the invention. The catheter 10 can be one of a variety of different catheters, but is preferably an intravascular catheter. Examples of intravascular catheters include balloon catheters, atherectomy catheters, drug delivery catheters, diagnostic catheters and guide catheters. Except as described herein, the intravascular catheter 10 can be manufactured using conventional techniques and materials.

The intravascular catheter 10 can be sized in accordance with its intended use. The catheter 10 can have a length that is in the range of about 50 centimeters to about 140 centimeters and can have a diameter that is in the range of about 3 F (French) to about 9 F.

In the illustrated embodiment, the intravascular catheter 10 includes an elongate shaft 12 that has a proximal region 14, a distal region 16 and a distal end 18. A hub and strain relief assembly 20 can be connected to the proximal region 14 of the elongate shaft 12. The hub and strain relief assembly 20 includes a main body portion 22, a pair of flanges 24 designed to improve gripping, and a strain relief 26 that is intended to reduce kinking. The hub and strain relief assembly 20 can be of conventional design and can be attached using conventional techniques.

FIG. 2 is a cross-sectional view of the elongate shaft 12, taken along line 2-2 of FIG. 1. The elongate shaft 12 includes an outer layer 28 and an inner layer 30. Each of the outer layer 28 and the inner layer 30 can extend from the proximal region 14 of the elongate shaft 12 to the distal region 16 of the elongate shaft 12. The inner layer 30 defines a lumen 32 that extends through the elongate shaft 12.

In some embodiments, as illustrated, the elongate shaft 12 can include a reinforcing braid or ribbon layer 34 to increase particular properties such as kink resistance. A reinforcing braid or ribbon layer 34 can be positioned between the outer layer 28 and the inner layer 30. The reinforcing braid or ribbon layer can be provided in a configuration that provides adequate kink resistance without substantially increasing the overall profile of the elongate shaft 12.

In some embodiments (not specifically illustrated), the elongate shaft 12 can include one or more shaft segments having varying degrees of flexibility. For example, the elongate shaft 12 can include a proximal segment, an intermediate segment and a distal segment. In some embodiments, the elongate shaft 12 can also include a distal tip segment that can be formed from a softer, more flexible polymer. The elongate shaft 12 can include more than three segments, or the elongate shaft 12 can include fewer than three segments.

If the elongate shaft 12 has, for example, three segments such as a proximal segment, an intermediate segment and a distal segment, each segment can include an inner layer 30 that is the same for each segment and an outer layer that becomes increasingly more flexible with proximity to the distal end 18 of the elongate shaft 12. For example, the proximal segment can have an outer layer that is formed from a polymer having a hardness of 72 D (Durometer), the intermediate segment can have an outer layer that is formed from a polymer having a hardness of 68 D and the distal segment can be formed from a polymer having a hardness of 46 D.

If the elongate shaft 12 has three segments, each of the segments can be sized in accordance with the intended function of the resulting catheter 10. For example, the proximal segment can have a length of about 35 inches, the intermediate segment can have a length that is in the range of about 2 inches to about 3 inches, and the distal segment can have a length that is in the range of about 1 inch to about 1.25 inches.

The inner layer 30 can be a uniform material and can define a lumen 32 that can run the entire length of the elongate shaft 12 and that is in fluid communication with a lumen (not illustrated) extending through the hub assembly 20. The lumen 32 defined by the inner layer 30 can provide passage to a variety of different medical devices, and thus the inner layer 30 can include, be formed from or coated with a lubricious material to reduce friction within the lumen 32. An exemplary material is polytetrafluoroethylene (PTFE), better known as TEFLON®. The inner layer 30 can be dimensioned to define a lumen 32 having an appropriate inner diameter to accommodate its intended use. In some embodiments, the inner layer 30 can define a lumen 32 having a diameter of about 0.058 inches and the inner layer 30 can have a wall thickness of about 0.001 inches.

The outer layer 28 can be formed from any suitable polymer that will provide the desired strength, flexibility or other desired characteristics. Polymers with low durometer or hardness can provide increased flexibility, while polymers with high durometer or hardness can provide increased stiffness. In some embodiments, the polymer material used is a thermoplastic polymer material. Some examples of some suitable materials include polyurethane, elastomeric polyamides, block polyamide/ethers (such as PEBAX®), silicones, and co-polymers. The outer layer 28 can be a single polymer, multiple layers, or a blend of polymers. By employing careful selection of materials and processing techniques, thermoplastic, solvent soluble, and thermosetting variants of these materials can be employed to achieve the desired results.

In particular embodiments, a thermoplastic polymer such as a co-polyester thermoplastic elastomer such as that available commercially under the ARNITEL® name can be used. The outer layer 28 can have an inner diameter that is about equal to the outer diameter of the inner layer 30.

In some embodiments, the outer layer 28 can have an inner diameter in the range of about 0.060 inches to about 0.070 inches and an outer diameter in the range of about 0.064 inches to about 0.078 inches. Part or all of the outer layer 28 can include materials added to increase the radiopacity of the outer layer 28, such as 50% bismuth subcarbonate.

FIGS. 3 through 8 illustrate medical devices formed by adhesively securing two components together using an aerated adhesive in accordance with embodiments of the present invention. The first and second components can generically represent any two medical device components that can be adhesively secured together. In some embodiments, the first and second components can individually represent, respectively, an elongate shaft 12 and a hub assembly 20 (see FIG. 1). In some embodiments, the first and second components can represent an elongate shaft 12 and a strain relief 26 (see FIG. 1). In some embodiments, the first and second components can represent a strain relief 26 and a hub assembly 20 (see FIG. 1).

In particular, FIGS. 3 through 5 illustrate an assembly 36 that includes a first component 38 and a second component 40. The first component 38 has an outer surface 42 that in part defines an outer engagement portion 44. Similarly, the second component 40 has an inner surface 46 that in part defines an inner engagement portion 48. The first component 38 defines a lumen 50. FIG. 4 is a cross-sectional view through the assembly 36 proximate the outer and inner engagement portions 44 and 48.

Each of the first component 38 and the second component 40 can be formed of any suitable material such as a polymeric material and can be formed to any suitable dimension, as discussed above with respect to FIGS. 1 and 2. As illustrated, each of the first component 38 and the second component 40 are cylindrical in shape, but in other embodiments, additional structures and shapes are contemplated.

In some embodiments, the first component 38 can have an overall length that is in the range of about 50 cm to about 140 cm, an inner diameter that is in the range of about 2 F to about 8 F and an outer diameter that is in the range of about 3 F to about 9 F. In some embodiments, the second component 40 can have an overall length that is in the range of about 1 inch to about 3 inches, an inner diameter that is in the range of about 3 F to about 10 F and an outer diameter that is in the range of about 4 F to about 11 F.

In the illustrated embodiment, the outer engagement portion 44 of the first component 38 has an outer diameter that is at least substantially the same as an outer diameter of the first component 38 beyond the outer engagement portion 44. The outer engagement portion 44 can have a length that is in the range of about 0.020 inch to about 0.500 inch. Similarly, the inner engagement portion 48 of the second component 40 has an inner diameter that is at least substantially the same as an inner diameter of the second component 40 beyond the inner engagement portion 48. The inner engagement portion 48 can have a length that is in the range of about 0.020 inch to about 0.500 inch.

In other embodiments, as will be discussed in greater detail hereinafter, the outer engagement portion 44 can have a decreased outer diameter. In other embodiments, the second component 40 can be configured to fit within the first component 40, and in this instance, the outer engagement portion 44 can have an increased diameter.

An aerated adhesive layer 52 is positioned between the outer engagement portion 44 and the inner engagement portion 48. The distance between the outer engagement portion 44 and the inner engagement portion 48 can vary, depending on the tolerances to which each of the first component 38 and the second component 40 are manufactured. In some embodiments, the distance between the outer engagement portion 44 and the inner engagement portion 48 can vary from about 0.001 inch to about 0.010 inch.

Therefore, in some embodiments, the aerated adhesive layer 52 can vary in thickness from about 0.001 inch to about 0.010 inch, and can have an average thickness that is in the range of about 0.002 inch to about 0.008 inch. In some embodiments, the assembly 36 can be formed by disposing an aerated adhesive over the outer engagement portion 44 of the first component 38, followed by disposing the inner engagement portion 48 of the second component 40 over the outer engagement portion 44.

In other embodiments, the assembly 36 can be formed by disposing the second component 40 over the first component 38 such that the inner engagement portion 48 overlies the outer engagement portion 44. An aerated adhesive can subsequently be injected into a void between the outer and inner engagement portions 44 and 48. The aerated adhesive can subsequently be cured to form the aerated adhesive layer 52.

In some embodiments, it can be advantageous to put together the assembly 36 under an inert atmosphere. Any suitable inert gas can be used, either at atmospheric pressure or at above-atmospheric pressure, but argon and nitrogen are preferred. In particular embodiments, the assembly 36 can be formed under a nitrogen gas atmosphere at a pressure that is in the range of about 2 psig to about 15 psig.

FIG. 5 is an axial cross-section taken through FIG. 4, better illustrating the aerated adhesive layer 52. The aerated adhesive layer 52 can include any suitable adhesive material. In particular, the aerated adhesive layer 52 can be formed from any suitable light-curable adhesive. Suitable examples include acrylic, epoxy, acrylic/epoxy, and acrylic/urethane based adhesives.

The aerated adhesive layer 52 includes a plurality of voids 54 that can be formed in a variety of ways. In some embodiments, the voids 54 can be formed by metering an inert gas into the adhesive stream while applying the adhesive to the surfaces to be joined.

Other methods of forming the voids 54 include metering the adhesive and inert gas through a mixing tube.

In some embodiments, the voids 54 can include an inert gas at ambient or above-ambient pressure. In particular embodiments, the voids 54 contain nitrogen gas at a pressure that is in the range of about 2 psig to about 15 psig.

The voids 54 can provide distensible regions within the aerated adhesive layer 52 that can distend or deform in response to stresses caused by the adhesive shrinking while curing. The voids 54 can vary in size, but in some embodiments the voids 54 can have an average diameter of about 0.001 inch. In some embodiments, the aerated adhesive layer 52 can include an amount of voids 54 that is in the range of about 25 to about 50 volume percent. The aerated adhesive layer 52 can have a density that is reduced by about 25 to about 50 percent with respect to a density of the adhesive itself without any aeration.

In some embodiments, it maybe useful for a completed assembly to have a constant outer diameter. FIG. 6 shows an assembly 55 having a constant outer diameter. The assembly 55 includes a first component 56 and a second component 58 that can be formed of any suitable material and to any suitable dimension, as discussed previously with respect to FIG. 3. The first component 56 has an outer surface 60 that in part defines an outer engagement portion 62. The second component 58 has an inner surface 64 that in part defines an inner engagement portion 66. An aerated adhesive layer 68 is disposed between the outer engagement portion 62 and the inner engagement portion 66.

As illustrated, the outer engagement portion 62 of the first component 56 has an outer diameter that is reduced with respect to an outer diameter of the first component beyond the outer engagement portion 62. In some embodiments, the outer engagement portion 62 can have an outer diameter that is reduced an amount substantially equal to the thickness of the inner engagement portion 66 of the second component 58 plus the thickness of the aerated adhesive layer 68. In some embodiments, the outer engagement portion 62 can have an outer diameter that is reduced about 35 to about 65 percent.

While not illustrated, in some embodiments, the outer engagement portion 62 can have an outer diameter that is reduced somewhat with respect to an outer diameter of the first component 56 beyond the outer engagement portion 62, and the inner engagement portion 66 can have an inner diameter that is increased somewhat with respect to an inner diameter of the second component 58 beyond the outer engagement portion 66.

In other embodiments, it may be useful for a completed assembly to have a lumen having at least a substantially constant diameter. FIG. 7 illustrates an assembly 70 that includes a first component 72 and a second component 74 that can be formed of any suitable material and to any suitable dimension, as discussed previously with respect to FIG. 3. The first component 72 has an outer surface 76 that in part defines an outer engagement portion 78. The second component 74 has an inner surface 80 that in part defines an inner engagement portion 82. An aerated adhesive layer 84 is disposed between the outer engagement portion 78 and the inner engagement portion 82.

The inner engagement portion 82 can have an inner diameter that is increased with respect to an inner diameter of the second component 74 beyond the inner engagement portion 82. In some embodiments, the inner engagement portion 82 can have an inner diameter that is sufficiently increased to accommodate a wall thickness of the outer engagement portion 78 and a thickness of the aerated adhesive layer 84. As a result, a lumen 86 extending through the assembly 70 can have at least a substantially constant diameter.

Figure 8:
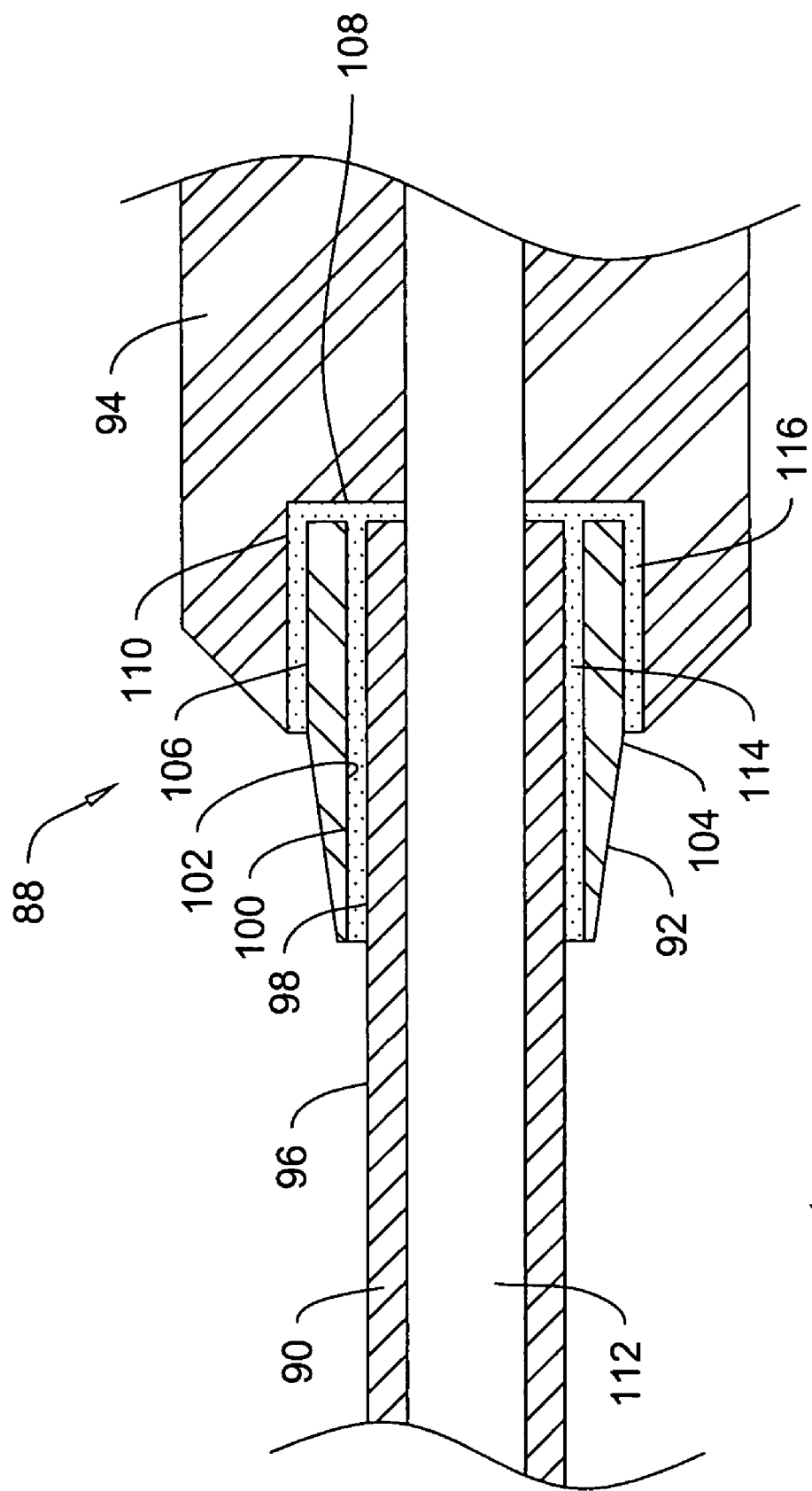
FIG. 8 is a partially-sectioned view of a medical device in accordance with an embodiment of the invention.

In some embodiments, several components can be secured together. FIG. 8 illustrates an assembly 88 that includes a first component 90, a second component 92 and a third component 94 that can be formed of any suitable material and to any suitable dimension, as discussed previously with respect to FIGS. 1-3. In some embodiments, the first component 90 can represent an elongate shaft, the second component 92 can represent a strain relief and the third component 94 can represent a hub or other connector.

In some embodiments, the first component 90 can have an overall length that is in the range of about 50 cm to about 140 cm, an inner diameter that is in the range of about 2 F to about 8 F and an outer diameter that is in the range of about 3 F to about 9 F. In some embodiments, the second component 92 can have an overall length that is in the range of about 1 inch to about 3 inches, an inner diameter that is in the range of about 3 F to about 10 F and an outer diameter that is in the range of about 4 F to about 11 F. In some embodiments, the third component 94 can have an overall length that is in the range of about 1 inch to about 2 inches, and an inner diameter that is in the range of about 3 F to about 11 F.

The first component 90 can have an outer surface 96 that in part defines an outer engagement portion 98. The second component 92 can have an inner surface 100 that defines in part an inner engagement portion 102 and can also have an outer surface 104 that defines in part an outer engagement portion 106. The third component 94 can have an inner surface 108 that in part defines an inner engagement portion 110. A lumen 112 can extend through the assembly 88.

A first aerated adhesive layer 114 can be disposed between the outer engagement portion 98 of the first component 90 and the inner engagement portion 102 of the second component 92. A second aerated adhesive layer 116 can be disposed between the outer engagement portion 106 of the second component 92 and the inner engagement portion 110 of the third component 94. In some embodiments, the first aerated adhesive layer 114 and the second aerated adhesive layer 116 can be separately formed, possibly of different aerated adhesives. In some embodiments, the first aerated adhesive layer 114 and the second aerated adhesive layer 116 can represent a single continuous aerated adhesive layer.

Medical devices as described herein can be partially or completely coated with a lubricious or other type of coating. Hydrophobic coatings such as fluoropolymers provide a dry lubricity that can improve handling and device exchanges. An example of a suitable fluoropolymer is polytetrafluoroethylene (PTFE), better known as TEFLON®.

Lubricious coatings can improve steerability and improve lesion crossing capability. Examples of suitable lubricious polymers include hydrophilic polymers such as polyarylene oxides, polyvinylpyrolidones, polyvinylalcohols, hydroxy alkyl cellulosics, algins, saccharides, caprolactones, and the like, and mixtures and combinations thereof. Hydrophilic polymers can be blended among themselves or with formulated amounts of water insoluble compounds (including some polymers) to yield coatings with suitable lubricity, bonding, and solubility. In some embodiments, a distal portion of a composite medical device can be coated with a hydrophilic polymer as discussed above, while the more proximal portions can be coated with a fluoropolymer.

The medical devices described herein can include, or be doped with, radiopaque material to improve visibility when using imaging techniques such as fluoroscopy techniques. Any suitable radiopaque material known in the art can be used. Some examples include precious metals, tungsten, barium subcarbonate powder, and the like, and mixtures thereof. In some embodiments, radiopaque material can be dispersed within the polymers used to form the particular medical device. In some embodiments, the radiopaque materials distinct from the ferromagnetic materials are dispersed.

It should be understood that this disclosure is, in many respects, only illustrative. Changes may be made in details, particularly in matters of shape, size, and arrangement of steps without exceeding the scope of the invention. The invention's scope is, of course, defined in the language in which the appended claims are expressed.

I claim:

1. A medical device, comprising:
   a first component having an outer surface including an outer engagement portion;
   a second component having an inner surface including an inner engagement portion, the inner engagement portion configured to fit over the outer engagement portion; and
   an aerated adhesive layer positioned between the inner engagement portion and the outer engagement portion, wherein the medical device is a catheter.

2. The medical device of claim 1, wherein the aerated adhesive layer resists delamination between the aerated adhesive layer, the inner engagement portion and the outer engagement portion.

3. The medical device of claim 1, wherein the aerated adhesive layer absorbs stresses resulting from curing of the aerated adhesive.

4. The medical device of claim 1, wherein the aerated adhesive layer comprises distensible regions.

5. The medical device of claim 1, wherein the aerated adhesive layer comprises a light-curable adhesive.

6. The medical device of claim 5, wherein the light-curable adhesive comprises an adhesive selected from the group consisting of acrylic, epoxy, acrylic/epoxy, and acrylic/urethane based adhesives.

7. The medical device of claim 1, wherein the aerated adhesive layer comprises a plurality of voids.

8. The medical device of claim 7, wherein the plurality of voids comprise at least about 25 percent volume of the aerated adhesive layer.

9. The medical device of claim 7, wherein the voids include an inert gas.

10. The medical device of claim 9, wherein the inert gas comprises $N_2$.

11. The medical device of claim 9, wherein the inert gas is at ambient pressure.

12. The medical device of claim 9, wherein the inert gas is at greater than ambient pressure.

13. The medical device of claim 1, wherein the aerated adhesive layer has an effective density that is about 25 to about 50 percent less than a density of the adhesive material itself.

14. The medical device of claim 1, wherein a gap between the outer surface of the first component and the inner surface of the second component is at least about 0.001 inch.

15. The medical device of claim 1, wherein the aerated adhesive layer has an average thickness that is in the range of about 0.002 inch to about 0.008 inch.

16. The medical device of claim 1, wherein the first component comprises an elongate shaft and the second component comprises a hub.

17. The medical device of claim 1, wherein the first component comprises an elongate shaft and the second component comprises a strain relief.

18. The medical device of claim 1, wherein the first component comprises a strain relief and the second component comprises a hub.

* * * * *